United States Patent [19]

Hobart et al.

[11] Patent Number: 5,312,398
[45] Date of Patent: May 17, 1994

[54] APPARATUS FOR DELIVERING A LASER BEAM

[75] Inventors: James L. Hobart, Los Altos Hills; David Trost, San Francisco, both of Calif.

[73] Assignee: Coherent, Inc., Palo Alto, Calif.

[21] Appl. No.: 867,895

[22] Filed: Apr. 13, 1992

[51] Int. Cl.⁵ .................... A61B 17/36; A61B 17/24
[52] U.S. Cl. .............................. 606/14; 128/4; 606/2; 606/17
[58] Field of Search ................... 606/2, 14–19; 128/395, 396, 4, 6

[56] References Cited

U.S. PATENT DOCUMENTS

| | | | |
|---|---|---|---|
| 1,675,364 | 7/1928 | Loeck | 128/4 |
| 3,918,438 | 11/1975 | Hayamizu et al. | 128/4 |
| 3,994,557 | 11/1976 | Hopkins | 128/4 X |
| 4,036,218 | 7/1977 | Yamashita et al. | 128/4 |
| 4,772,116 | 9/1988 | Schöder et al. | 128/395 X |
| 4,963,143 | 10/1990 | Pinnow | 606/14 |

FOREIGN PATENT DOCUMENTS 2511131 9/1976 Fed. Rep. of Germany ........ 606/14
2033649 5/1980 United Kingdom ................ 606/18

Primary Examiner—Peter A. Aschenbrenner
Attorney, Agent, or Firm—Limbach & Limbach

[57] ABSTRACT

A beam delivery apparatus, including a set of focusing mirrors (or transmissive lenses) mounted along an endoscope channel. A laser beam can be focused into an input end of the channel with a smaller F number (wider cone angle) than is possible in a conventional endoscope. As the beam propagates down the channel, it is reflected (or transmitted) a finite number of times by the focusing elements. The focusing elements act as a periscope to focus and refocus the beam as it propagates along the channel, with little loss of beam power. The invention enables delivery of the beam to the channel's distal end with a smaller F number than can be achieved using a conventional endoscope. In a preferred embodiment, a pair of reflecting strips are mounted the channel, the surface of each strip defines six focusing mirrors, and the beam undergoes a total of twelve reflections from the mirrors as it propagates down the channel. Preferably, the surface of each mirror has a curvature selected to prevent the introduction of astigmatic distortion during each beam reflection.

10 Claims, 2 Drawing Sheets

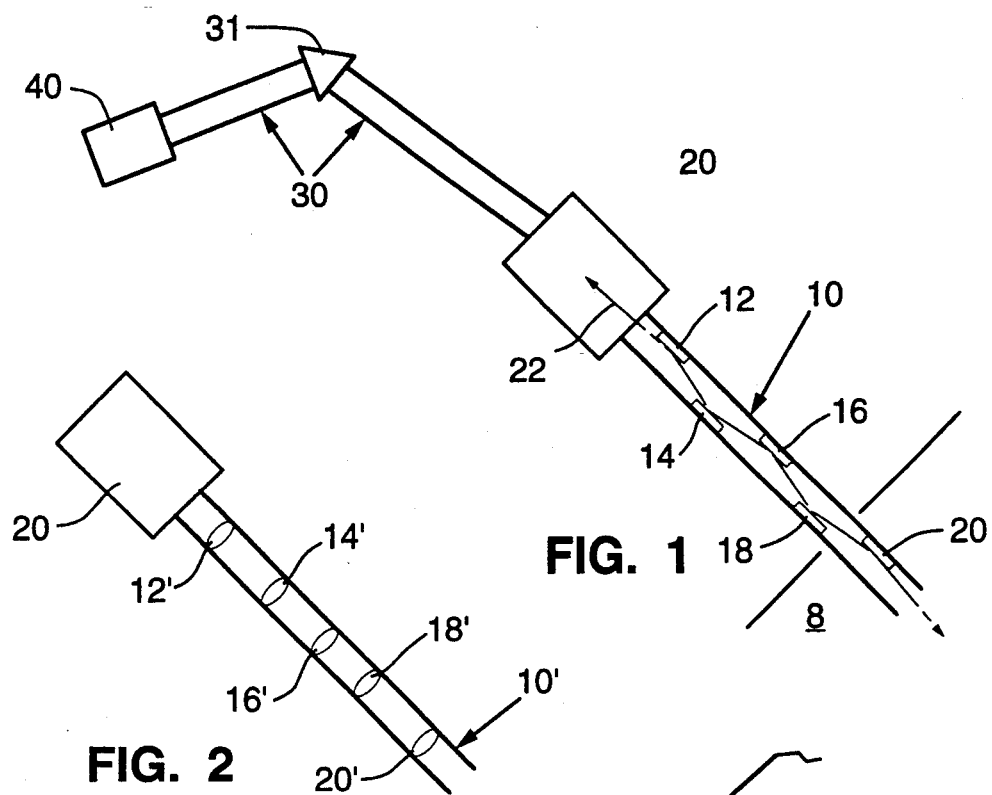
FIG. 1
FIG. 2
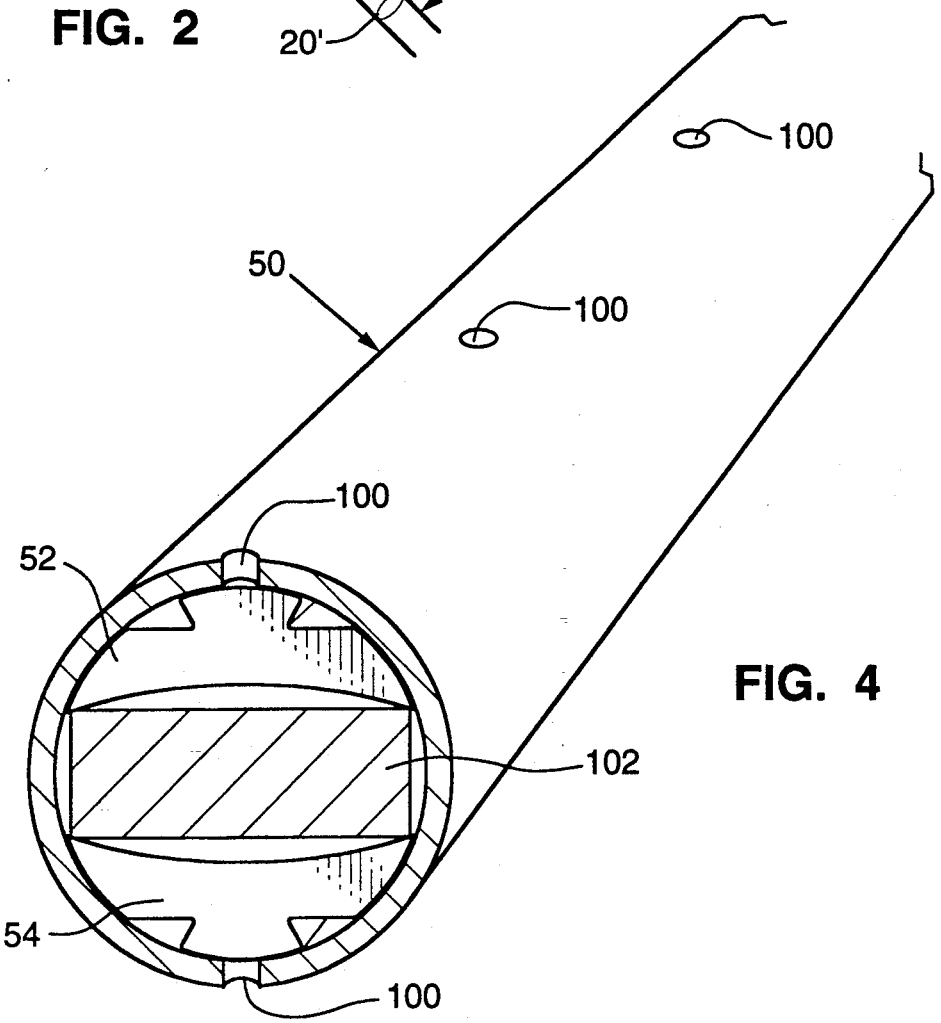
FIG. 4

APPARATUS FOR DELIVERING A LASER BEAM

FIELD OF THE INVENTION

The invention pertains to a laser beam delivery apparatus. More particularly, the invention pertains to an apparatus for delivering a laser beam through a channel, such as the channel of a laparoscope.

BACKGROUND OF THE INVENTION

In the technique known as laparoscopic surgery, a surgeon gains access to an abdomen or other body cavity through a small incision, typically having length on the order of one centimeter. A laparoscope is inserted through the incision into the body cavity.

The laparoscope has an open channel extending through it (typically 30 to 40 centimeters in length, with a diameter in the range 5 to 7 millimeters). The surgeon can insert a surgical instrument (such as the beam of a laser) through the channel, and gas (such as carbon dioxide) can also be introduced through the channel (for insufflation). A conventional laparoscope also includes a train of viewing optics (typically having diameter in the range 2 to 5 millimeters) to facilitate imaging of the body cavity.

In a conventional technique for delivering a laser beam through a laparoscope (or another type of endoscope), a direct coupler introduces the beam into the input end of the laparoscope (or endoscope) channel. The direct coupler (which is essentially a long focal length lens) receives the beam from the end of an articulated arm assembly, and directs the beam into the laparoscope (or endoscope). The beam is introduced into the articulated arm assembly by a laser (typically a $CO_2$ laser which emits radiation having a wavelength of 10.6 microns). An apparatus employing such a direct coupler is described in U.S. Pat. No. 4,917,083, issued Apr. 17, 1990, with reference to FIG. 3.

However, conventional systems using direct couplers have a number of serious limitations and disadvantages. One such disadvantage is that the beam often strikes the walls of the laparoscope (or endoscope) channel as a result of angular misalignment of the beam at the channel entrance. This often results in a scattered and ineffective output beam at the channel's distal end, and in undesirable heating of the channel walls.

Another disadvantage resulting from use of direct couplers in conventional systems is due to the fact that in such systems the F number of the beam cannot be smaller than the ratio L/w, where L is the length of the channel and w is the diameter of the channel. Since the beam's spot size at the channel's distal end is proportional to the F number, a small spot cannot be produced at the distal end when the beam is simply focused into the channel by a direct coupler. This problem is enhanced when gas (such as carbon dioxide gas) flows through the channel, since the gas absorbs power from the beam, thereby reducing the output beam power at the channel's distal end, and forming a thermal lens (which in turn enlarges the beam's spot size at the channel's distal end).

Waveguides have been employed in some conventional laparoscopes (and endoscopes) to deliver a laser beam into a body cavity. A waveguide is a small diameter tube whose walls are highly reflective to laser radiation that strikes the walls while propagating down the tube. Examples of waveguides include optical fibers (filled with solid transparent material) and hollow waveguides (sometimes referred to as "air fibers" or "air core waveguides"). U.S. Pat. No. 4,805,987, issued Feb. 21, 1989, discloses a flexible, hollow waveguide of a type which could conceivably be employed in a laparoscope or an endoscope.

In the endoscope described in above-cited U.S. Pat. No. 4,917,083, a waveguide receives laser radiation focused by a direct coupler.

Use of a waveguide to deliver a laser beam has the serious disadvantage that a waveguide tends to degrade the beam quality (defined as the ratio of the F number of the beam to the spot size at focus). The result is that the spot size at focus is maintained over a much shorter depth of focus than can be achieved by propagating a precisely oriented beam parallel to the central axis of a channel (without reflection from the channel side walls). This short depth of focus limits the beam's usefulness to a surgeon.

While waveguides can in principle deliver a beam with little loss of beam quality, in practical applications this desired result is very difficult to achieve due to the practical limitations of mechanical and optical tolerances. Furthermore, when gas flows through a hollow waveguide, the same problems described above with reference to direct couplers will result, due to absorption of beam power by the gas flowing within the waveguide. Of course, if a solid waveguide is employed (rather than a hollow waveguide), gas cannot flow through the waveguide at all, which additionally limits the utility of the laparoscope (or endoscope) to the surgeon.

Throughout the remaining portion of the specification, including in the claims, the term "endoscope" will be used in a broad sense to denote laparoscopes and other types of endoscopes.

Until the present invention, it was not known how to eliminate the described disadvantages and limitations of conventional apparatus for coupling a laser beam into, and delivering the beam through, an endoscope channel.

SUMMARY OF THE INVENTION

The invention is a beam delivery apparatus including a set of focusing mirrors (or transmissive lenses) mounted along an endoscope channel. A laser beam is focused into an input end of the channel with a smaller F number (wider cone angle) than is possible in a conventional endoscope. As the beam propagates down the channel, it is reflected (or transmitted) a finite number of times by the focusing elements. The focusing elements act as a periscope to focus and refocus the beam as it propagates along the channel, with little loss of beam power. The invention enables delivery of the beam to the channel's distal end with high quality and a smaller F number than can be achieved using a conventional endoscope.

In a preferred embodiment, two reflecting strips are mounted to the channel wall. The surface of one strip is shaped to define six focusing mirrors, the surface of the other strip is shaped to define five focusing mirrors and a flat mirror, and the beam undergoes a total of twelve reflections from the mirrors as it propagates down the channel from mirror to mirror. Preferably, the surface of each mirror has a curvature selected to prevent the introduction of astigmatic distortion during each beam reflection.

Both a treatment beam and a viewing beam can be transmitted down a single endoscope channel which embodies the invention. Alternatively, the endoscope can include two separate channels, one or both of which embody the invention, and the treatment beam and the viewing beam can be transmitted down different ones of the channels.

BRIEF DESCRIPTION OF THE DRAWINGS

FIG. 1 is a schematic diagram of a beam delivery apparatus, including an endoscope which embodies the invention.

FIG. 2 is a schematic diagram of an alternative embodiment of the inventive endoscope.

FIG. 4 is a perspective view of the FIG. 3 apparatus with a spacer member (of the type used during the process of manufacturing the apparatus) inserted therein.

DETAILED DESCRIPTION OF THE PREFERRED EMBODIMENT

Figure 3:
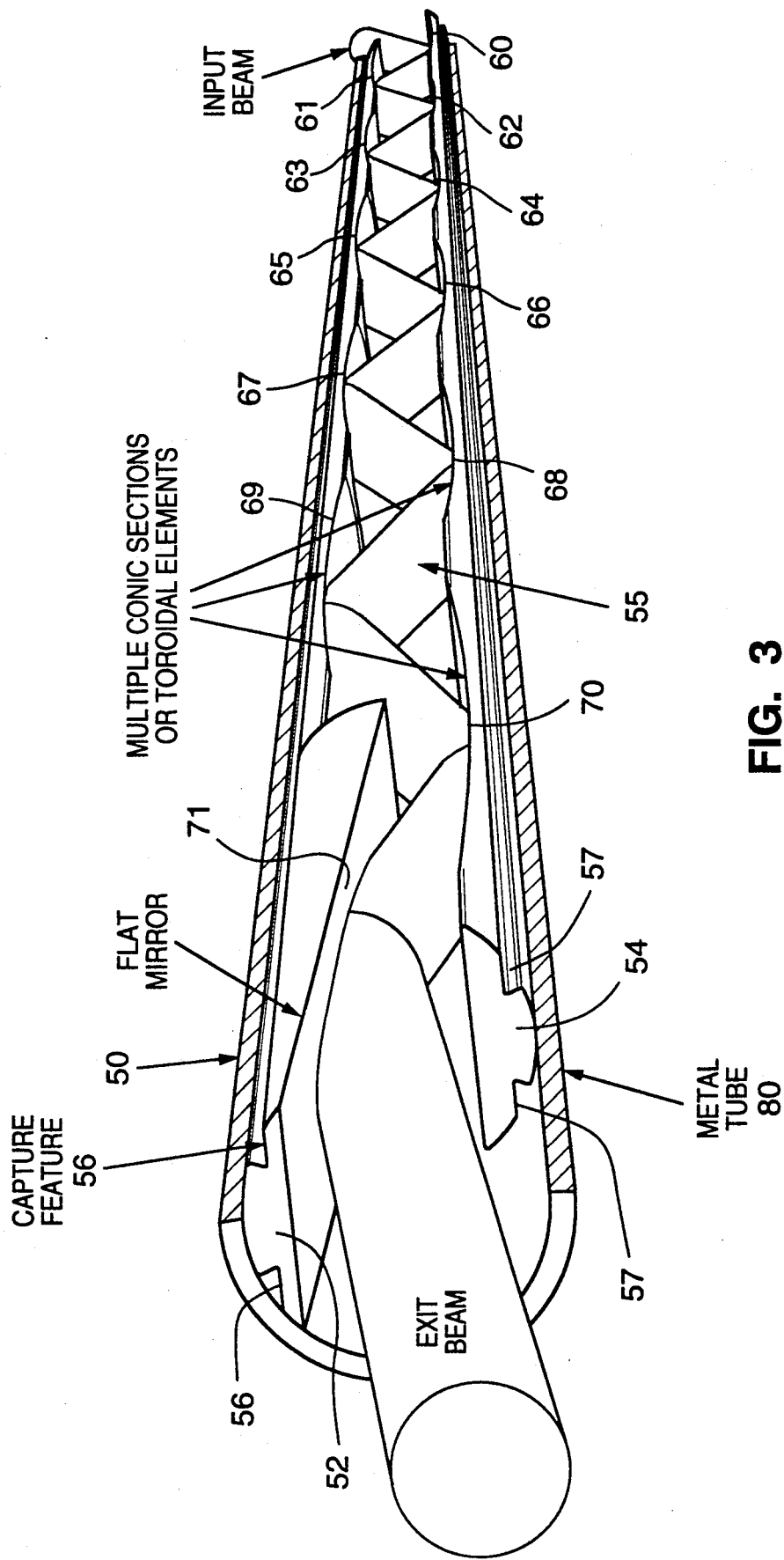
FIG. 3 is a cut-away, perspective view of an endoscope designed in accordance with a preferred embodiment of the invention.

A first embodiment of the invention will be described with reference to FIG. 1. In FIG. 1, articulated arm assembly 30 connects laser 40 with direct coupler 20. Corner mirror assembly 31 connects the two rigid tubular arms of assembly 30. One end of endoscope 10 is connected to coupler 20. The opposite end of endoscope 10 (the "distal" end) is inserted into body cavity 8.

A set of focusing mirrors (including mirrors 12, 14, 16, 18, and 20) is mounted along the open channel extending through endoscope 10. The open channel has central longitudinal axis 22, and has a small diameter (typically in the range from 5 to 7 millimeters).

A beam of coherent radiation from laser 40 propagates through arm assembly 30 and coupler 20, into endoscope 10. Focusing mirrors 12, 14, 16, 18, and 20 are mounted in staggered fashion so that the beam reflects successively from the mirrors 12, 14, 16, 18, and 20, as it propagates along the open channel through endoscope 10 into cavity 8. Coupler 20 directs the beam toward the first focusing mirror (mirror 12) with a grazing incidence angle. Preferably, the other mirrors are positioned (relative to the first focusing mirror) so that they successively receive the reflected beam with grazing incidence.

A variation on the FIG. 1 embodiment will next be described with reference to FIG. 2. In FIG. 2, endoscope 10' includes a set of lenses 12', 14', 16', 18', and 20' (i.e., a set of transmissive focusing elements rather than a set of focusing mirrors as in endoscope 10 of FIG. 1. The FIG. 2 apparatus can deliver a high quality beam (with a long depth of focus) to the distal end of an endoscope channel, by successively refocusing the beam at elements 12' through 20'.

For most applications (particularly where the laser beam consists of infrared radiation), use of reflective focusing elements as in FIG. 1 is preferable to use of transmissive elements as in FIG. 2 because transmissive elements tend to be more expensive and fragile than reflective elements having corresponding focusing power. Due to the small diameter of a typical endoscope channel, the transmissive elements needed to implement the FIG. 2 embodiment will usually be very small. When a high power beam is focused through such a set of small lenses, the lenses can easily become overheated and damaged. Furthermore, lenses (such as elements 12' through 20') mounted within an endoscope channel will fully obstruct the channel, making it impossible for the channel to function as a flow channel for insufflation gas.

In a variation on the FIG. 2 embodiment, endoscope 10' includes a second open channel (not shown in FIG. 2) through which gas can flow to the patient's body cavity.

Endoscope 50 of FIG. 3 is a preferred embodiment of the inventive apparatus. Endoscope 50 comprises rigid metal tube 80 through which an open channel extends. Reflecting strips 52 and 54 are fixedly mounted within tube 80 in the open channel. Each reflecting strip has an elongated surface shaped to define one or more (smaller) mirror surfaces. Strip 54 defines focusing mirror surfaces 60, 62, 64, 66, 68, and 70. Strip 52 defines focusing mirror surfaces 61, 63, 65, 67, and 69, and flat mirror surface 71.

A laser beam is received at the end of tube 80 adjacent mirror surface 60 (typically from an articulated arm assembly as in FIG. 1). The beam is incident at mirror surface 60 with a grazing incidence angle, reflects from surface 60 to surface 61, and then reflects from surface 61 to surface 62. The reflected beam continues to reflect successively from surfaces 62, 63, 64, 65, 66, 67, 68, 69, 70, and 71. After reflecting from the final mirror surface 71, the beam exits the distal end of tube 80. The beam's path through the tube (identified by reference numeral 55) is shown in FIG. 3.

Each of focusing mirrors 60-70 has a reflective surface with two different curvatures. The mirror surfaces can have toroidal curvature, or the intersection of a plane with each mirror surface can be a conic section (for example, a parabola or an ellipse). In a class of preferred embodiments, each of surfaces 60-70 is designed to focus (as well as reflect) a beam incident at the surface with a selected incidence angle, without introducing astigmatism into the reflected beam.

One way to design suitably shaped embodiments of each of surfaces 60-70 employs the following formulae:

$$fx = [Rx \cos(I)]/2 \qquad (1)$$

$$fy = Ry/[2 \cos(I)] \qquad (2)$$

where Rx and Ry are the radii of curvature of the surface in the XZ and YZ planes, I is the angle of incidence of the principal ray, and fx and fy are focal lengths in the XZ and YZ planes. Formulae (1) and (2) can be solved for the radii in terms of the focal lengths as follows:

$$Rx = (2fx)/\cos(I) \qquad (3)$$

$$Ry = 2fy[\cos(I)] \qquad (4)$$

To design and construct a mirror surface having the same focal length in the XZ and YZ planes, the necessary radii Rx and Ry can readily be calculated from formulae (3) and (4).

As an example, consider a design in which the incidence angle I is 84.3 degrees (which is a grazing incidence angle), and the desired focal length is $fx = fy = 50$ mm. Using formulae (3) and (4), the radii of curvature are found to be $Rx = 1000$ mm and $Ry = 10$ mm. The mirror surface in this example has the appearance of a long, narrow, scalloped indentation, as does surface 70 in FIG. 3.

The final mirror surface encountered by the beam before exiting tube 80 (i.e., mirror 71 in the FIG. 3 embodiment) is preferably flat.

Since reflecting strips 52 and 54 are thin, and do not protrude far from the inner wall of tube 80, they do not seriously obstruct the flow of gas down the tube. The mirror surfaces can be manufactured to be much more tolerant of high laser power than transmissive optics. Another desirable feature of the inventive design is that the typical grazing incidence of the beam at each mirror surface will distribute the beam power over an area on each mirror surface that is approximately one order of magnitude greater than the area of an optic that would be exposed to a beam with normal incidence. This further improves the ability to withstand high power and contamination. The flow of insufflation gas down tube 80 further reduces the susceptibility of the apparatus to contamination, both by limiting the ability of contaminants to enter the tube against the aerodynamic force of the flowing gas, and by providing cooling action to hot spots on the mirror surfaces that may develop due to contamination.

Due to the very small diameter of conventional endoscope channels (typically, in the range from 5 to 7 millimeters), each of strips 52 and 54 typically must have a very small cross-section in order to fit within such a channel without excessively obstructing the channel. It is generally difficult to fabricate and handle optical elements having such a small cross section. To alleviate this problem, in a preferred embodiment, the back surface of strip 52 has a pair of capture features 56 (indentations), and the back surface of strip 54 has a pair of similar indentations 57. Indentations 56 and 57 enable the strips to be conveniently handle during fabrication (such as during the process of applying suitable reflective coatings to the front surface of each strip).

During fabrication of endoscope 50, strips 52 and 54 can be glued to opposite sides of the inner cylindrical wall of tube 80. To conveniently accomplish this, two rows of glue holes 100 are drilled through tube 80, one for each strip. One row of such glue holes 100 (for strip 52) is shown in FIG. 4. The strips are then inserted within tube 80 in alignment with the glue holes, and are held in position by spacer member 102 (shown in FIG. 4) which is inserted into tube 80 between the strips. Glue is then injected through holes 100 to bond the strips to tube 80. After the glue cures, spacer member 102 is removed.

The number of mirror surfaces that are positioned along the endoscope channel in accordance with the invention, and the shape of each mirror surface, will depend on the length and diameter of the channel, the expected incidence angle of the beam at the channel's input end, and the wavelength of the beam.

The beam propagating through tube 80 may include two or more different frequency components, for example, a low power visible component for imaging the patient's body cavity, and a high power infrared component for performing surgery (or otherwise treating the patient).

Alternatively, the endoscope can include two separate open channels (for example, two cylindrical tubes), and a different beam can propagate through each channel (i.e., a treatment beam through one channel and a viewing beam through the other channel). One or both of the channels may embody the invention.

Various modifications and alterations in the structure and method of operation of this invention will be apparent to those skilled in the art without departing from the scope and spirit of this invention. Although the invention has been described in connection with specific preferred embodiments, it should be understood that the invention as claimed should not be unduly limited to such specific embodiments.

What is claimed is:

1. A beam delivery apparatus, including:
   an endoscope having a channel extending therethrough, wherein the channel has an input end and an output end and a central longitudinal axis; and
   a set of beam focusing mirrors fixedly mounted along the channel, for successively refocusing a laser beam as the beam propagates along the channel from the input end to the output end, wherein the set of beam focusing mirrors includes a pair of reflective strips attached to opposite sides of the channel, wherein each of the strips has a longitudinal axis oriented substantially parallel to the central longitudinal axis, and wherein the surface of each strip defines at least one focusing mirror.

2. The apparatus of claim 1, wherein each of the focusing mirrors has a surface having a curvature in each of a first direction and a second direction orthogonal to the first direction, and wherein the curvature in each of said first direction and said second direction is selected to prevent introduction of astigmatic distortion during reflection of the beam from said each of the focusing mirrors.

3. The apparatus of claim 1, wherein the surface of at least one of the strips defines at least one toroidal mirror.

4. The apparatus of claim 1, wherein each of the focusing mirrors has a curved surface, and wherein the intersection of a plane with each said curved surface is a conic section.

5. The apparatus of claim 1, wherein a first one of the reflective strips defines six focusing mirrors, and a second one of the strips defines five focusing mirrors and a flat mirror.

6. The apparatus of claim 1, wherein each of the reflective strips has a back surface with a pair of indentations therein.

7. The apparatus of claim 1, also including:
   means positioned at the input end of the channel for directing the laser beam into the input end of the channel toward the beam focusing mirrors with a grazing incidence angle.

8. An endoscope for transmitting a beam of radiation, comprising:
   an elongated member having an axial channel with an input opening at one end and at exit opening at the other end;
   a first set of reflecting elements mounted along one surface of the channel; and
   a second set of reflecting elements mounted on the opposed surface of the channel, said reflecting elements being positioned so that a beam entering the input opening will be directed down the channel to the exit opening by alternately reflecting off elements in the first set and the second set.

9. The endoscope of claim 8, wherein said reflecting elements have curvatures configured to minimize astigmatic effects.

10. The endoscope of claim 8, wherein each of the reflecting elements has a toroidal curvature.

* * * * *